(12) United States Patent
Geron et al.

(10) Patent No.: US 7,582,256 B1
(45) Date of Patent: Sep. 1, 2009

(54) AIR PURIFICATION WALL

(75) Inventors: Laurent Geron, Les Waleffes (BE); René Winand, Rixensart (BE); Leila Dehbi, Martigues (FR)

(73) Assignee: Arcelormittal France (FR)

( * ) Notice: Subject to any disclaimer, the term of this patent is extended or adjusted under 35 U.S.C. 154(b) by 0 days.

(21) Appl. No.: 10/574,047

(22) PCT Filed: Sep. 30, 2004

(86) PCT No.: PCT/BE2004/000138
§ 371 (c)(1),
(2), (4) Date: Feb. 27, 2007

(87) PCT Pub. No.: WO2005/030372
PCT Pub. Date: Apr. 7, 2005

(30) Foreign Application Priority Data
Oct. 1, 2003 (EP) .................................. 03447240

(51) Int. Cl.
*A61L 9/16* (2006.01)
(52) U.S. Cl. .................. 422/4; 422/24; 422/121; 422/122
(58) Field of Classification Search .............. None
See application file for complete search history.

(56) References Cited

U.S. PATENT DOCUMENTS 5,925,320 A * 7/1999 Jones ................... 422/121
6,048,499 A 4/2000 Hirayama
2004/0136863 A1 * 7/2004 Yates et al. ............... 422/4

FOREIGN PATENT DOCUMENTS

| EP | 590477 | 4/1994 |
|---|---|---|
| EP | 993859 | 4/2000 |
| JP | 09-000941 | 1/1997 |
| JP | 09-084866 | 3/1997 |
| JP | 10-249166 | 9/1998 |
| JP | 2000-051332 | 2/2000 |
| JP | 2000257185 | 9/2000 |
| JP | 2000334448 | 12/2000 |
| JP | 2001218820 | 8/2001 |
| JP | 2001293336 | 10/2001 |
| JP | 2002035599 | 2/2002 |
| JP | 2002083511 | 3/2002 |
| JP | 2002295874 | 10/2002 |

* cited by examiner

*Primary Examiner*—Elizabeth L McKane
(74) *Attorney, Agent, or Firm*—Reinhart Boerner Van Deuren P.C.

(57) ABSTRACT

The invention relates to an appliance for the continuous photocatalytic purification of the air in a room, said appliance preferably being in the form of a wall (1) and comprising an external steel structure, an opening (11) for the admission of the air to be processed, an internal metallic framework (4) to which a plurality of UVA lamps (3) are fixed, a photocatalytic filter (2), and an opening (12) for discharging the purified air. The inventive appliance is characterised in that the photocatalytic filter comprises at least one metal grating (2) covered by a film containing titanium dioxide ($TiO_2$), mainly in an anatase phase, in order to maximise the surface of the photocatalyst illuminated by the UVA light.

20 Claims, 7 Drawing Sheets

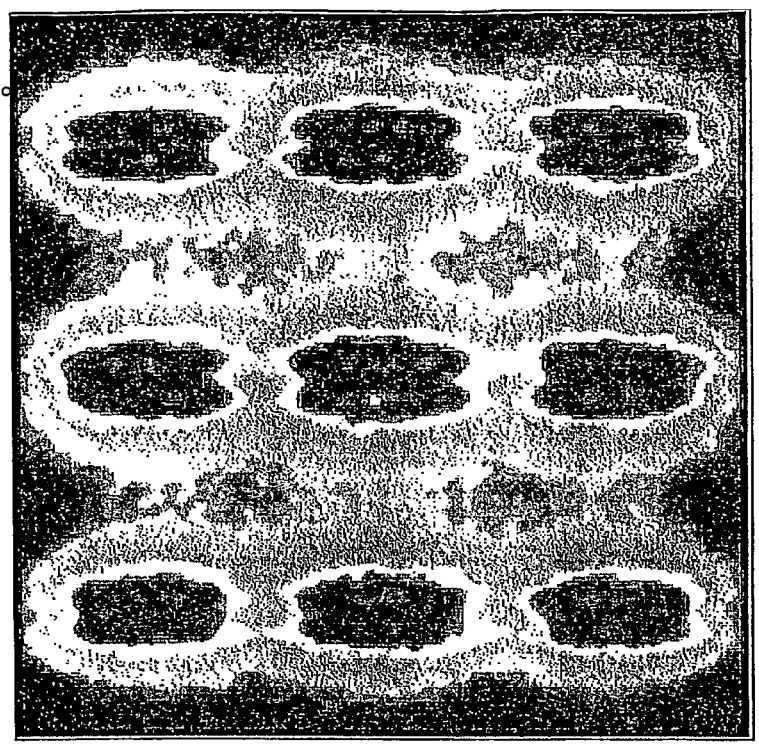
FIG.5a
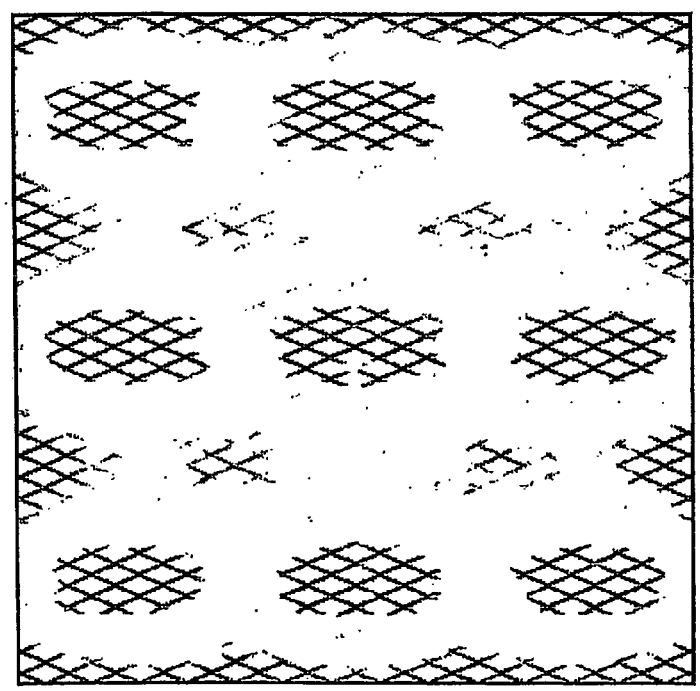
FIG.6
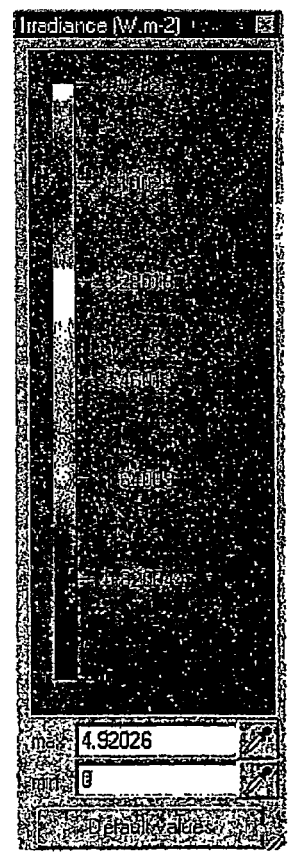

AIR PURIFICATION WALL

CROSS-REFERENCE TO RELATED PATENT APPLICATIONS

This patent application is the National Stage of International Application No. PCT/BE2004/000138 filed Sep. 30, 2004, that claims the benefit of European Application No. 03447240.7 filed Oct. 1, 2003.

FIELD OF THE INVENTION

The present invention relates to an air purification device working on the principle of heterogeneous photocatalysis upon contact with titanium dioxide and preferably taking the form of a wall panel.

The invention also relates to the method of air purification implemented by said device.

TECHNOLOGICAL BACKGROUND AND STATE OF THE ART

Heterogeneous photocatalysis is known since the 70's as a result of studies on the photo-induced dissociation of water. This technique consists in irradiating a semiconductor, usually of titanium dioxide, by natural sunlight or by artificial UV illumination, ($\lambda$<400 nm). This material undergoes excitation which allows an electron $e^-$ of the valence band to be ejected in the conduction band of the semiconductor (reduction). The corresponding hole $h^+$ (oxidation) may react with an OH group adsorbed on the surface of the semiconductor in order to form highly oxidising hydroxyl radicals OH. These are capable of reacting with organic molecules, for example pollutants, leading to the mineralization of the latter with the formation of water and carbon dioxide. Photocatalysis is an acceleration of the photoreaction due to the presence of the catalyst. It is heterogeneous since the photoreactions are generated at the interface between two environments that are in different phases at the surface of the catalyst.

Titanium dioxide $TiO_2$ exists in different crystalline forms: rutile, anatase, brookite and a large number of phases obtained by high pressure. Only the rutile and anatase crystalline forms show photocatalytic activity. In particular, anatase, the most active form, which was used in the frame of the present invention, has an elongated tetrahedral structure with irregular octahedrons of oxygen.

Titanium dioxide is present in great quantity, whether in paints, cosmetics, foodstuffs, etc. Its photoactivity thus allows to use it in order to decompose organic molecules adsorbed on its surface. Heterogeneous photocatalysis upon contact with titanium dioxide was therefore used in particular for the purification of water, destruction of pollutants, pesticides, dyes, bacteria, detoxification of agricultural and industrial rinsing waters, air purification (deodorisation, elimination of toxic gases) and as self-cleaning agent for objects or buildings in the open air, exposed to the elements.

A very large number of air purification and/or deodorisation devices with a photocatalytic filter based on $TiO_2$, some of which also have a structural or architectural function, have been proposed. In most cases, the problems solved by these inventions are:

- optimisation of the use of UV irradiation, as a result for example of the optimisation of the geometry and arrangement between the photocatalytic support and the lamps or by increasing the effectiveness of a UV lamp regarding its photocatalytic effect by the addition of reflectors (see for example JP 09 084866, EP 993859, JP 2000 334448, JP 10 249166, JP 2001 293336, JP 2002 295874, JP 2001 218820);
- increase in the range of spectral light usable for catalytic activity, for example the use of visible light in applications of the photocatalytic light type (see for example JP 2002 083511, JP 2002 035599);
- improvement in the maintenance of the devices resulting from the easier replacement of the lamps;
- increase in compactness by the use of flat lamps or light-emitting diodes (LEDs) rather than traditional UV lamps (see for example JP 2000 051332, JP 09 000941).

In most cases, the patented device is provided with a fan to force the circulation of air, the airflow possibly being made turbulent.

However, the devices according to the state of the art are of little or no assistance in meeting the following requirements:

- incorporation of the air purifier as an architectural element requires for one thing, structural mechanical properties of the assembly that are satisfactory and for another, great compactness in terms of depth, which is difficult to achieve given the need to place the UV lamps with the correct orientation;
- maximization of the surface of the photocatalytic filter achieved by UV illumination;
- optimisation of the air circulation inside the device;
- temperature regulation of the external walls of the device.

AIMS OF THE INVENTION

The present invention aims to provide a solution that overcomes the drawbacks of the state of the art.

The invention aims to provide an air purifier incorporated into the construction elements of buildings at the level of their wall panels.

In particular, the invention also aims to provide an air purifier working as an open loop so as to continuously remove pollution from the atmosphere of an inhabited space.

MAIN CHARACTERISTIC ELEMENTS OF THE INVENTION

One first object of the present invention relates to a continuous photocatalytic purification device for the air of an inhabited room, preferably taking the form of a wall panel, comprising:

- an external metal structure, preferably made of steel;
- an opening for the intake of the air to be treated located in the lower portion of the front part of the wall;
- an internal metal frame to which a series of UVA lamps are attached, i.e. lamps emitting ultraviolet radiation in the range of 315-400 nm;
- a filter comprising a support covered by a film with photocatalytic titanium dioxide ($TiO_2$);
- an opening for the outlet of the purified air located in the upper portion of the front part of the wall, the airflow inside the device being ensured by natural circulation or forced circulation with at least one fan;

characterised in that said device comprises at least one grate made of expanded metal covered by a film with titanium dioxide ($TiO_2$), mainly in the anatase phase, so as to maximise the surface of the photocatalyst illuminated by the UVA light.

The present invention has the advantage over the state of the art that the support of the photocatalytic filter is made of metal and therefore has an unlimited working life in contrast to the paper supports usually used.

The ambient air purification device according to the invention is preferably intended for the destruction of volatile organic compounds such as alkanes, alcohols, aldehydes, ketones, aromatics and terpenes by photocatalysis upon contact with titanium dioxide.

This device is more generally intended to be used in the building industry, in the form of a structural or decorative element such as for example a wall panel, dividing wall, floor, ceiling, false ceiling, etc. The structural element having an external metal surface is advantageously compatible with all types of covering finish such as plaster, paint, wallpaper, etc.

As an advantage, the external metal structure is either made of a steel such as a bright-annealed stainless steel or it has an internal surface covered by a thin layer with a reflective index greater than 90% for wavelengths shorter than 400 nm.

Maximising for one thing, the total surface illuminated and for the other, the power absorbed per unit of surface area of the filter has the advantage of allowing a significant reduction in the illumination power required and therefore the heating and the operation cost, and in the final analysis optimises efficiency.

According to a preferred embodiment of the invention, the front part of the external structure has a width of at least 1.5 meters, preferably 2 meters, the openings for the intake and outlet of air being in the form of slits of equal width and of a slightly smaller width than that of said front part and of a height greater than 3 cm, preferably equal to 5 cm.

Said openings are preferably located at least 10 cm, even more preferably 5 cm, from the bottom and top ends respectively of said front part.

One essential characteristic of the invention being to maximise the surface of expanded metal, preferably expanded steel, covered by a photocatalyst, the whole mesh surface of this expanded steel ($S_{steel}$) is covered by the $TiO_2$ film, with the exception of the surface of the mesh thickness, i.e.:

$$S_{steel} = \left[ w s_{mesh} \sqrt{\left(\frac{LD_{mesh}}{2}\right)^2 + \left(\frac{SD_{mesh}}{2}\right)^2} - \frac{st_{mesh}^2}{2\sin\left(2\arctg\left(\frac{SD_{mesh}}{LD_{mesh}}\right)\right)} \right],$$

where $LD_{mesh}$, $SD_{mesh}$ and $st_{mesh}$ are the long diagonal, the short diagonal and the strips of the mesh, respectively.

In order to further increase this advantage, the mesh is selected so as to minimise the ratio ($S_{steel}$) between its physical surface ($S_{steel}$) and its total surface ($S_{mesh}$):

$$s_{steel} = \frac{S_{steel}}{S_{mesh}} = \frac{4}{LD_{mesh} SD_{mesh}} S_{steel}$$

said ratio preferably being ⅓.

According to preferred embodiments of the invention, the grate is vertically maintained with fixings located only on the perimeter of the grate, the UVA lamps are arranged in series of three across the width of the wall, the fan is of a tangential type set at 90° and is located at the top of the wall, the number of fans being selected to ensure that at least 30 m³/hour/person of air is renewed in the inhabited room.

According to yet another preferred embodiment of the invention, the air purification device may take the form of a cylinder of circular, rectangular or square cross-section with at least one UVA lighting tube along the axle of the cylinder and surrounded by an expanded metal grate covered with photocatalytic $TiO_2$, the internal surface of the cylinder having a reflective index greater than 90%. This embodiment is more specifically intended for the purification of air or for the removal of pollution from the air in a duct.

A second object of the present invention relates to a method for optimising the sizing of an air purification element as detailed above, this method being characterised by the following steps:

a) definition of the external geometry of the device;
b) definition of the number of expanded steel grates and of the illumination device;
c) calculation of the illumination of the grates; if the light intensity is not greater than the set tolerance threshold, return to step b);
d) calculation of the airflow and of the temperature distribution; if the steel walls heat up, return to step b);
e) calculation of the change in the concentration of pollutants; if overall purification efficiency is not greater than the predefined limit, return to step b);
f) achieving the optimum dimensions for the purification or pollution removal element.

SHORT DESCRIPTION OF THE FIGURES

FIG. 1 schematically shows a three-dimensional view of the air purification wall according to the present invention.

FIG. 2 schematically shows an exploded view of the active wall according to the invention.

FIG. 3 schematically shows a mesh, the basic unit of an element made of expanded metal, on which titanium dioxide is deposited.

FIG. 4 schematically shows the modification of the flow in a tangential fan set at 90°.

FIG. 5.a shows the raw illumination chart calculated on an expanded metal grate belonging to the air purifier according to the invention.

FIG. 5.b shows examples of profiles with raw light intensity reaching the grate of expanded metal in terms of direct and indirect illumination.

FIG. 6 shows the chart of light intensity used in the purification model associated to the present invention.

Figure 8:
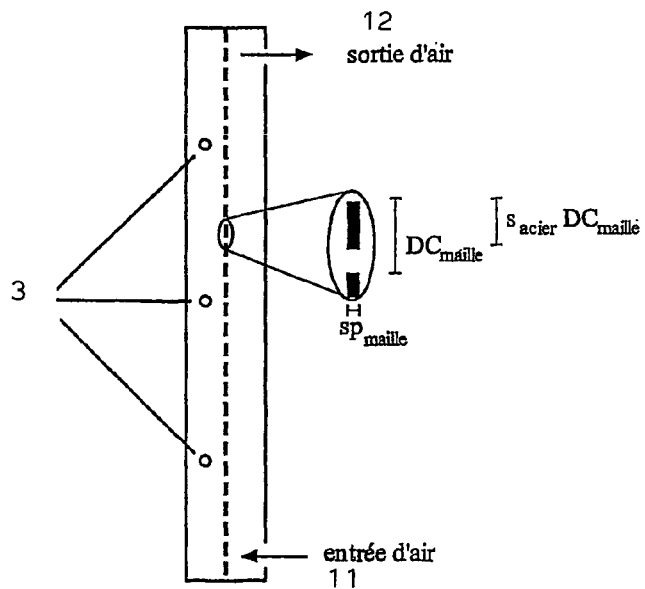

FIG. 8 schematically shows an example of a two-dimensional model of a purification wall comprising a grate and three lamps.

Figure 9:
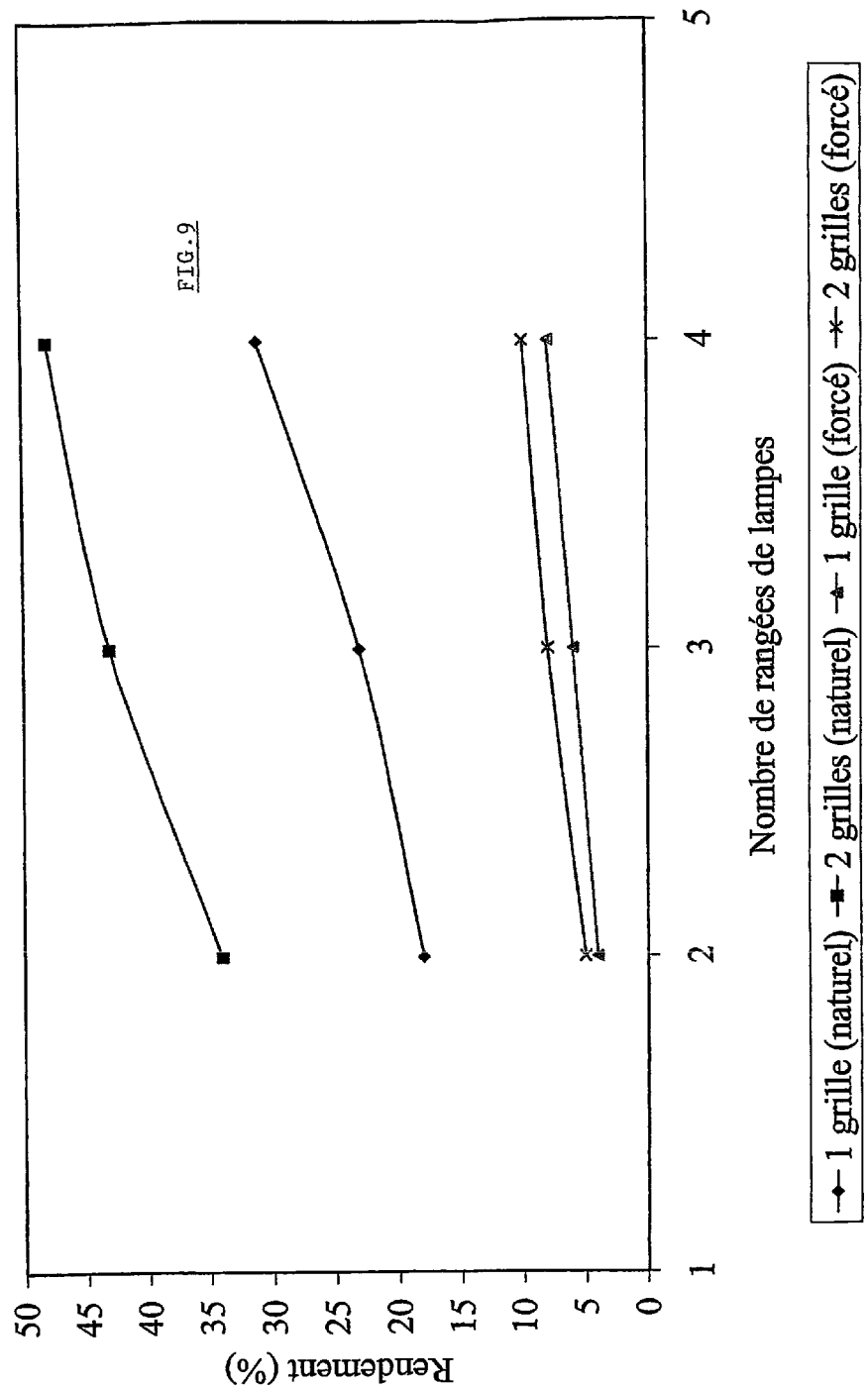

FIG. 9 graphically shows the efficiency of the purification wall according to the present invention as a function of the number of grates, the number of series of lamps and the type of air circulation (natural or forced).

Figure 10:
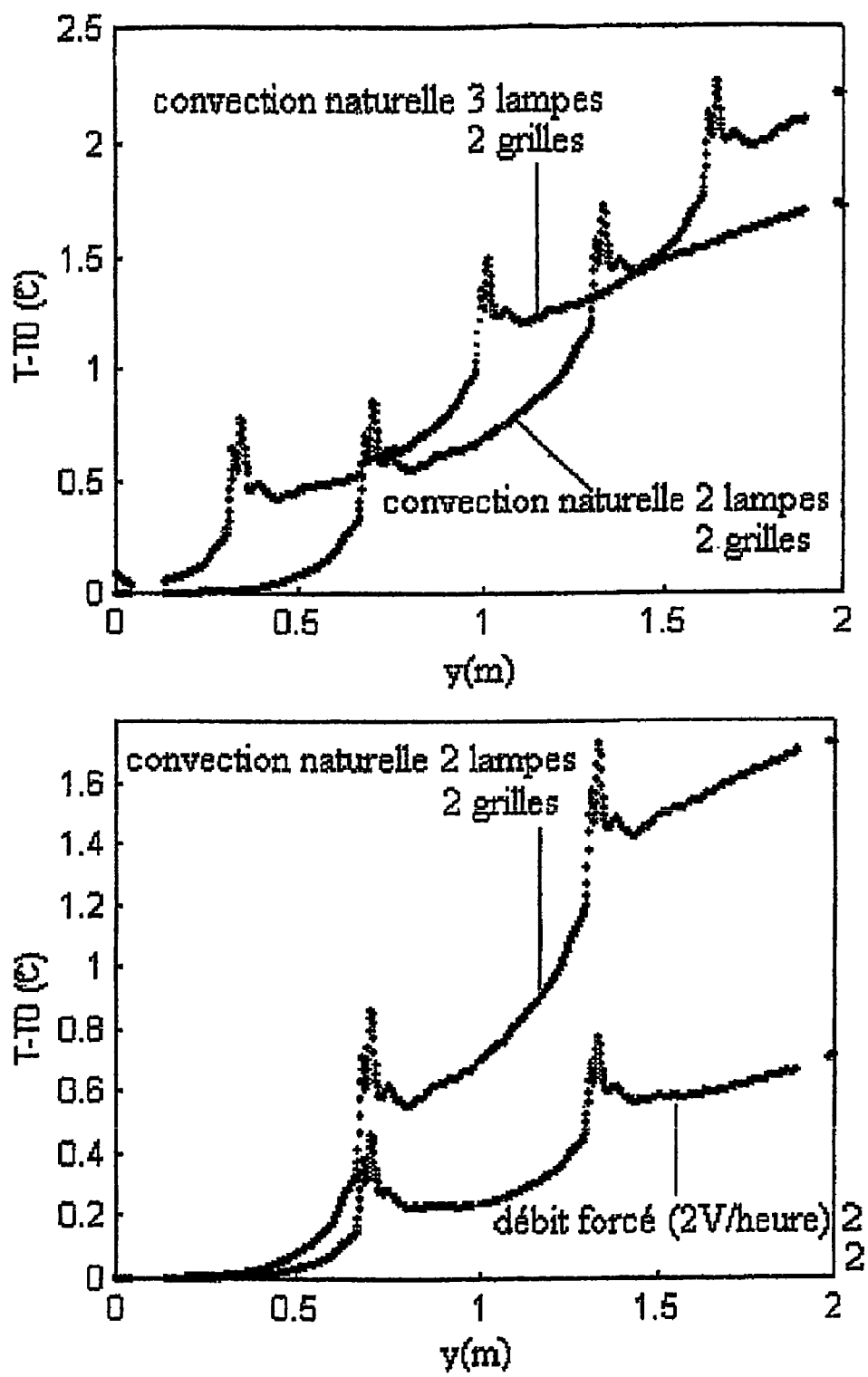

FIG. 10 shows profiles of temperature on the external facings of the purification wall as a function of the number of UVA lamps and of the type of flow assumed.

DESCRIPTION OF A PREFERRED
EMBODIMENT OF THE INVENTION

Figure 1:
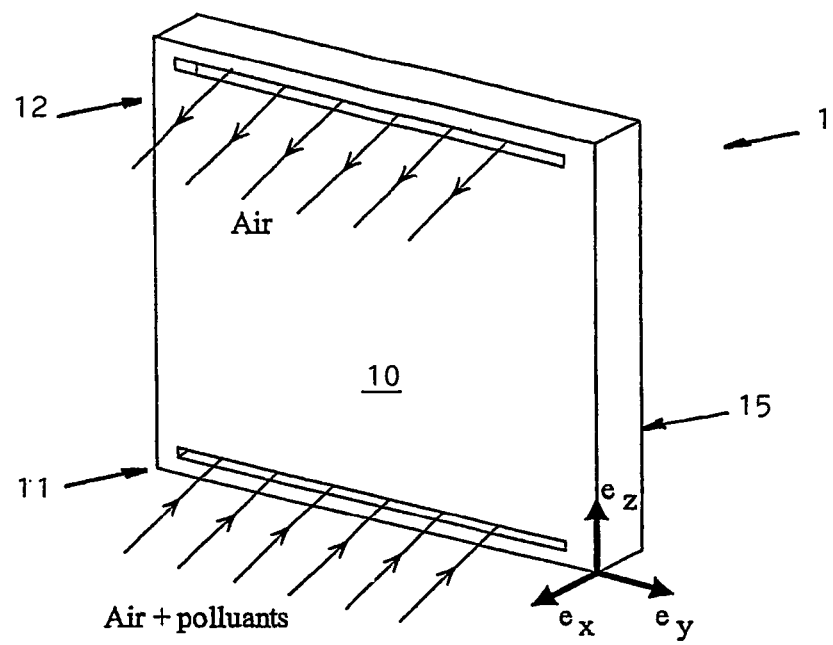
Figure 2:
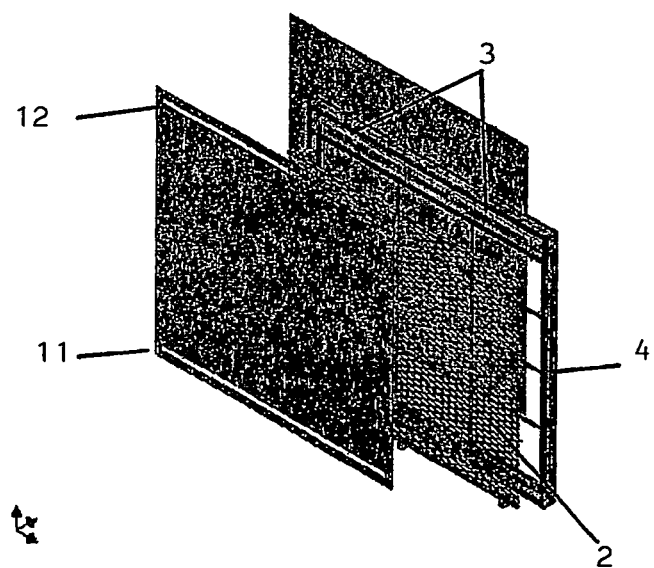

The air purification wall 1 shown on FIGS. 1 and 2 works on the known principle of heterogeneous photocatalysis upon contact with titanium dioxide. This device comprises an active wall 1 operating as an open loop that comprises:

an air intake 11 located at the bottom of the front part 10 of the wall through which the mix of air and any possible pollutant enters the device;

inside the wall, one or several grates 2 made of expanded steel, on which titanium dioxide is deposited, illuminated by an illumination device with UVA lamps 3 for the activation of the $TiO_2$ film;

an opening 12 located at the top of the front part 10 of the wall through which the air, cleaned from its pollutants, is ejected. The airflow is generated either by fans (convection or forced circulation) or by the increased temperature as a result of the illumination system (natural circulation).

In order to optimally size the air purification device according to the invention, mathematical and numerical models were used, in particular to describe the thermal and turbulent convective flow generating the circulation of the pollutants in the wall. A theoretical purification model developed for this specific case and checked by means of experimental results was introduced at the level of the limiting conditions in order to evaluate the efficiency of the purification device as regards pollution removal.

The overall study of the design and sizing of the wall must hence take into account the thermal, acoustic and structural constraints and the purification phenomena. The study achieved mainly focuses on the thermal aspect and on pollution removal.

In the context of sizing the wall, the calculation of the flow, of the temperature distribution and the purification process must be introduced in an overall optimisation algorithm without decoupling. The reason for this coupling is made clear by the definition of the sizing criteria.

The purification wall 1 is positioned in a confined space such as an office, a meeting room, etc. The ambient temperature in this space is therefore linked to the temperature of the steel wall acting as a limiting condition. Moreover, the potential direct contact between the people occupying the space and the wall requires to regulate the surface temperature of the steel. As a result, the first optimisation criterion is the minimisation of the heating up of the wall.

The second optimisation criterion is the efficiency of the purification process. The overall efficiency of photocatalysis must be maximised so as to reduce the time required for purifying the inhabited space under consideration.

These two criteria give rise to an optimisation function that has an extreme value. Indeed, to satisfy the first criterion, it is necessary to reduce the heating of the wall by the illumination system and, if necessary, try to make it reach zero. For the second criterion, there must be a photon flux sufficient to maximise the overall efficiency of the purification process and therefore to intensify the illumination system. The optimum consists in determining the illumination system that causes minimal heating whilst retaining maximum purification efficiency.

Figure 5B:
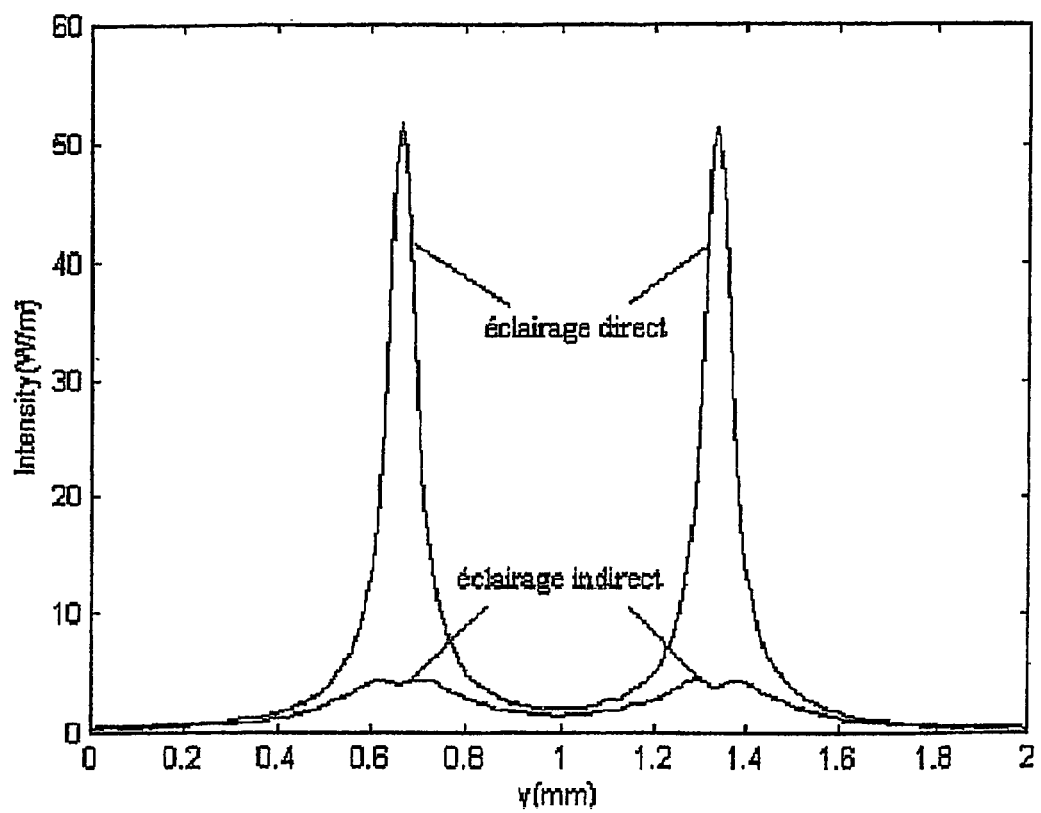

For the calculations, the external dimensions of the wall 1 being fixed at 2 meters high ($H_{wall}$), 2 meters wide ($W_{wall}$) and 10 cm thick ($t_{wall}$), the three parameters on which the sizing may be optimised are: the number of grates 2 of expanded metal, the number of UVA lamps 3 used in the illumination system and the use of (a) fan(s) 5 to force the flow (see for example FIG. 5).

As shown on FIG. 2, the active steel wall used comprises an assembly of elements each having a particular function allowing to obtain an optimised system of air purification by photocatalysis: the external steel structure, basically the front part 10 and the back part 15, the expanded metal grates 2 on which a $TiO_2$ film is deposited, the illumination system with the UVA lamps 3 attached to a metal frame 4. The assembly is completed by fans 5 and an electric box supplying the entire wall with power (not shown).

1. The External Structure

The external structure of the active wall 1 comprises plates of steel. The surface properties of these plates have a major role in terms of illuminating the titanium dioxide.

In order to achieve optimum efficiency of the photocatalysis upon contact with titanium dioxide, all expanded metal grates must be illuminated with an ultraviolet light from the different lamps making up the illumination system. To do so, the internal surfaces of the steel facings of the external structure must have a maximum reflective index for wavelengths shorter than the reference wavelength of anatase titanium dioxide, i.e. 387 nm. A steel with a reflective index in the ultraviolet that is high (higher than 90%) must therefore be used, for example bright-annealed stainless steel.

According to the preferred embodiment implemented, the front part 10 of the external structure has two openings 1.9 meters long and 5 cm high. The opening 11 located at the bottom of the front part 10 allows the air to enter the wall and to undergo heterogeneous photocatalysis upon contact with titanium dioxide and hence to be purified.

The opening 12 located at the top of the front part 10 allows the purified air to be fed back into the space that is to be treated.

The dimensions of the openings are determined according to several parameters: the volume of air treated, the time that the air remains in the wall and the speed of the air at the intake and outlet of the wall.

In order to maximise the volume of air treated by the active wall, the surface of the intake opening 11, located at the bottom of the front part, must be as large as possible. A length of 1.9 meters was therefore opted for, which satisfies the mechanical constraints in terms of the strength of the front part and the constraints in terms of the volume of air to be treated. The length of the outlet opening 12 is equal to the length of the intake opening 11 because, in order to achieve maximum purification efficiency, the airflow in the wall must be horizontally uniform, which is precisely obtained with equal intake and outlet lengths.

In order to maximise the time that the air remains in the active wall, it is essential to place the intake and outlet as far apart as possible. The intake opening was therefore placed 5 cm from the bottom of the active wall and the outlet opening 5 cm from its top.

According to IAQ standards, average acceptable air speeds in buildings are of the order of 20 to 30 cm/s. Moreover, the rate of air renewal for one person is of the order of 30 $m^3$/hr. In order to satisfy these two conditions, the height of the openings 11, 12 is defined as 5 cm.

2. The Expanded Metal Grates

The expanded metal grates 2 form the support of the semiconductor used for the heterogeneous photocatalysis process. In the study achieved, titanium dioxide mainly in the anatase phase was considered.

Figure 3:
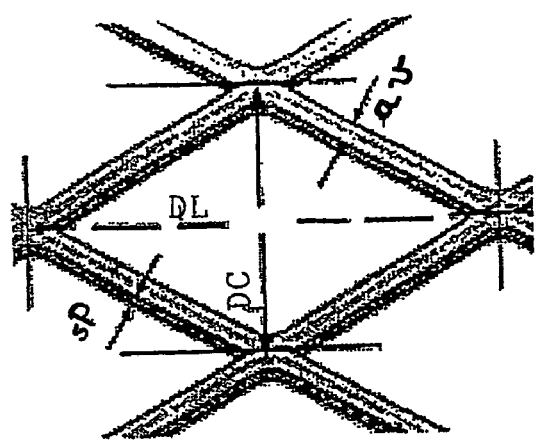

The expanded metal is defined as a matrix with the mesh 6 as basic element (see FIG. 3).

This mesh 6 is defined by four parameters: the long diagonal ($LD_{mesh}$), the short diagonal ($SD_{mesh}$), the width of the strips ($ws_{mesh}$) and the thickness ($th_{mesh}$). On the basis of the first three parameters, the metal surface of a mesh ($S_{steel}$) may be defined as:

$$S_{steel} = \left[ws_{mesh}\sqrt{\left(\frac{LD_{mesh}}{2}\right)^2 + \left(\frac{SD_{mesh}}{2}\right)^2} - \frac{ws_{mesh}^2}{2\sin\left(2\arctg\left(\frac{SD_{mesh}}{LD_{mesh}}\right)\right)}\right], \quad (1.1)$$

In order to define the four parameters of the expanded metal, several parameters must be taken into account: the total surface of the titanium dioxide film and the illumination of this surface by means of the illumination system.

In order to achieve optimum purification efficiency, the total surface of the $TiO_2$ film must be maximised. When $TiO_2$ is deposited on the expanded metal, the surface covered with $TiO_2$ is equal to the metal surface ($S_{steel}$). This equality of both surfaces is correct if no titanium dioxide is deposited on the thickness of the mesh 6. Based on the industrial method of deposition that will have to be used, this hypothesis is considered valid. Indeed, for an industrial application, the deposition of titanium dioxide will be achieved on a continuous steel sheet before it is expanded, which therefore implies the absence of titanium dioxide on the thickness of the mesh.

Moreover, in order to maximise the heterogeneous photocatalysis process upon contact with titanium dioxide, the entire surface of the semiconductor must be illuminated with the UVA light from the illumination system. With the active wall possibly having several expanded metal grates, it is therefore necessary that the light can reach both surfaces of each grate. To do so, the ratio between the physical surface of the mesh ($S_{steel}$) and the surface of the mesh ($S_{mesh}$) must be minimal:

$$s_{steel} = \frac{S_{steel}}{S_{mesh}} = \frac{4}{LD_{mesh} \cdot SD_{mesh}} S_{steel} \quad (1.2)$$

In order to satisfy these two requirements, a ratio of $S_{steel}$ of the order of 1/3 was opted for.

Based on the catalogue of expanded metal from the company MDB (Metal Déployé Belge S. A., Arcelor Group), three acceptable metals were selected, their references are 62.25.43.30, A28.15.21.10 and A28.15.25.15 and correspond to the following dimensions, respectively: ($LD_{mesh}$=62 mm, $SD_{mesh}$=25 mm, $ws_{mesh}$=4.3 mm, $th_{mesh}$=3 mm), ($LD_{mesh}$=28 mm, $SD_{mesh}$=15 mm, $ws_{mesh}$=2.5 mm, $th_{mesh}$=1 mm), ($LD_{mesh}$=28 mm, $SD_{mesh}$=15 mm, $ws_{mesh}$=2.5 mm, $th_{mesh}$=1.5 mm).

The last selection criterion for the expanded metal type depends on its structural rigidity. The expanded metal grates are vertically placed in the active wall. To avoid cluttering up the wall with internal reinforcement, the expanded metal used must be able to be maintained vertical with fixings only on the perimeter of the grate.

This criterion allows to make a final choice of 62.25.43.30 as the expanded metal since it has sufficient thickness to meet the rigidity criterion.

3. The Illumination System

The illumination system comprises a set of 25 W UVA lamps of type CLEO 2 (Philips). This type of lamp has a power output of 4.3 W in UVA, i.e. for wavelengths between 320 and 400 nm. They also produce UVB radiation with a ratio to the UVA of 1.2%. Their size is 516.9 mm long and 16 mm diameter.

The lamps are arranged in series of three along the width of the wall ($W_{wall}$). The number of series is determined during the calculation of the wall sizing. The criteria allowing to determine the number of series are: achieving minimum heating of the air and of the external structure of the wall and achieving a minimum illumination threshold of all the surfaces of the expanded metal grates on which titanium dioxide is deposited.

4. The Fans

The fans 5 ensure the circulation of the air through the active wall. The airflow generated by the fans must meet the standards for air renewal. The standards recommend an air renewal of the order of 30 $m^3$/hour/person for inhabited spaces.

Adjustment of the airflow may be envisaged depending on the type of space to be purified.

Tangential fans set at 90° are used, i.e. fans allowing to modify the direction of flow by 90°, of the Ziehl-Abegg brand and of type QR 06-GKM70PB. This type of fan allows important flows of the order of 550 $m^3$/hr.

The flow rate is adjusted by means of a potentiometer controlling the electric power supplied to the engine.

Figure 4:
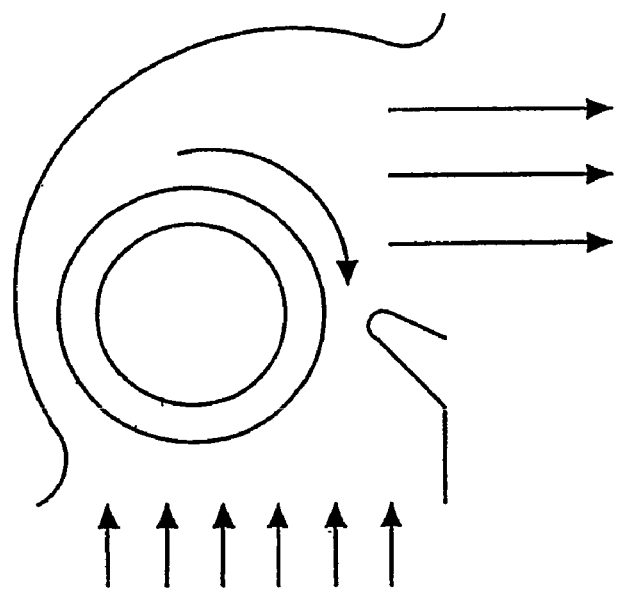

FIG. 4 shows the modification of the flow direction in a tangential fan set at 90°.

The fans are placed at the top of the active wall so as to achieve uniform flow throughout the wall.

5. The Electric Box

The operation of the active wall requires a source of electricity to supply the illumination system and the fans. In order to avoid the need for an electric plug for each lamp and for each fan, an electric box is installed in a lower corner. This electric box is supplied by a single electric plug from outside and provides the energy required for all electric components of the wall.

6. Flow and Limiting Conditions

In order to model the flows, the Navier-Stokes incompressible and stationary equations are used. The thermal effects on the flow are also introduced into the model by the Boussinesque approximation. The Reynolds number, defined by the flow rate of air in the wall and the intake surface, is large enough to justify the use of a turbulence model.

The slow flow speeds, of the order of 1 m/s, and the low level of heating of the wall validate the hypothesis required for the use of the incompressible approach and the Boussinesque approximation.

6.1 Dynamic Limiting Conditions

The flow rate of air must be applied at the intake for the purification device.

Two dynamic limiting conditions must be applied to the air intake. The flow rate of air $Q_{air}$, which will be varied during the numerical study, and the flow direction, that is assumedly perpendicular to the intake surface, are introduced.

At the outlet, only one limiting condition is required. The value of the reference pressure is applied.

6.2 Limiting Turbulent Conditions

At the intake to the purification device, a condition for the turbulent kinetic energy (k) and the dissipation of the turbulent kinetic energy (e) must be applied. These conditions are very difficult to evaluate since they depend on the flow upstream from the intake of the device, that flow is not modelled in the numerical simulations.

To define the limiting conditions, we reason in terms of the aim of the study. In this study concerning the sizing of the purification wall, the efficiency of the device must be evaluated in terms of air purification. It may be shown that the mixing of the air favours the purification process since it ensures optimum delivery of the pollutant to the surface of the semiconductor. This mixing of air is mainly characterised by the level of turbulence: the greater the turbulence, the more the pollutant is homogenised.

In order to study the most critical case, i.e. the case where mixing is minimal, we assume that the flow is laminar at the intake of the purification device. The turbulence is generated only inside the wall. The limiting conditions to be applied at the intake for the turbulent kinetic energy and its dissipation thus become very simple. The turbulent kinetic energy and its dissipation are cancelled.

6.3 Limiting Thermal Conditions

For the limiting thermal conditions, four different conditions are defined: the limiting condition at the intake of the purification device, the limiting condition on the lamps, the limiting condition on the internal parts of the wall and the limiting condition on the various parts of the expanded metal grates with the titanium dioxide.

The general expression of a limiting thermal condition incorporates the convective flow, radiative flow, conductive flow and external flow. This general expression is simplified as a function of the surface considered.

A) The Intake of the Purification Device

This limiting condition is the simplest. It will allow to determine the average temperature level in the purification wall. To do so, a temperature of 20° C. is applied.

$$T_{intake} = 20° \text{ C}. \tag{1.3}$$

B) The Lamps

The energy input is ensured by a system of 25 W lamps of CLEO type that ensure an illumination power of 4.3 W. The limiting condition on each lamp is:

$$k_0 \frac{d}{d\vec{n}} T \bigg|_{plate} + q''_{radiative} + q''_{lamps} = 0 \tag{1.4}$$

where the thermal flow of the lamps is given by the expression:

$$q''_{lamps} = \frac{P}{S_{lamps}} = \frac{4.3}{2\pi R_{lamp} L_{lamp}} = 147 \text{ W/m}^2 \tag{1.5}$$

where $R_{lamp}$ is the radius of the lamp (8 mm) and $L_{lamp}$ is the length of the lamp (517 mm).

C) The Internal Parts of the Wall

The limiting thermal condition on the wall is very complicated since the conductive exchanges inside the plate of bright-annealed stainless steel and the convective and radiative exchanges outside the wall must be taken into account. This type of data may not be precisely defined.

Two solutions may be envisaged: using coefficients of average external convective and radiative exchange or assuming the least favourable case for sizing the purification device. The second solution is opted for. Indeed, if a purification wall can be obtained with minimal heating in the least favourable conditions, all cases can certainly be covered.

Let us analyse the least favourable case. When the illumination system with UV lamps of CLEO type is operating in the wall, the expanded metal grates and the plates of bright-annealed stainless steel heat up. The front part of the wall is in direct contact with the temperature of the ambient air in the adjacent space. There is therefore a thermal transfer from the front part to the adjacent space. The adjacent space therefore tends to reduce the temperature of the front part. The least favourable case would be to assume that the air of the adjacent space immediately reaches the value of the temperature of the front part: this condition is a condition of adiabaticity. The possibility of external illumination of the front part that would logically raise the temperature is not taken into account.

The condition of adiabaticity is used, i.e. assuming that the sum of the conductive flow in the front part and of the external convective and radiative flows are zero.

The limiting condition is thus:

$$k_0 \frac{d}{d\vec{n}} T \bigg|_{plate} + q''_{radiative} + \alpha_{stainless} q''_{light} = 0 \tag{1.6}$$

where $q''_{light}$ is the light flux reaching the surface from the lamps and $\alpha_{stainless}$ is the absorption coefficient of the bright-annealed stainless steel.

The absorption coefficient of the bright-annealed stainless steel is of the order of 0.15 in the infrared and reaches a value of the order of 0.3 in the ultraviolet.

D) The Expanded Metal Grates

The expanded metal grates are completely incorporated in the calculation. A coupled type of limiting condition with additional input due to the energy input from the illumination system is therefore used.

7. Pollutants and Theoretical Purification Model

The purification device, the purification wall, must operate for complex mixes made up of a wide range of pollutants. Pollutants are grouped under the generic name of the volatile organic compounds (VOCs). Standards regulating the levels of pollution in buildings impose limits with regard to each pollutant but also to the total quantity of volatile organic compounds (TVOC). The average concentrations allowed are of the order of 200-500 µg/m³. This concentration level corresponds to values below the $ppm_{volume}$ for each pollutant.

The main pollutants are classified into 6 categories: alkanes, alcohols, aldehydes, ketones, aromatics and terpenes.

The first category of pollutants is that of alkanes. Alkanes are molecules solely made up of a carbon chain to which hydrogen atoms are bonded (Table 1).

TABLE 1

| Alkane | Formula | $C_A$ (µg/m³) | $MW_A$ (g/mol) | $C_A$ ($ppb_{volume}$) |
|---|---|---|---|---|
| Hexane | $C_6H_{14}$ | 9.85 | 86.2 | 2.56 |
| Heptane | $C_7H_{16}$ | 12 | 100.23 | 2.68 |
| Octane | $C_8H_{18}$ | 10.1 | 114.26 | 1.98 |
| Nonane | $C_9H_{20}$ | 8.5 | 128.29 | 1.48 |
| Decane | $C_{10}H_{22}$ | 15.7 | 142.32 | 2.47 |
| Undecane | $C_{11}H_{24}$ | 20.85 | 156.35 | 2.98 |
| Dodecane | $C_{12}H_{26}$ | 12.05 | 170.38 | 1.58 |
| Tridecane | $C_{13}H_{28}$ | 3.8 | 184.41 | 0.46 |
| Tetradecane | $C_{14}H_{30}$ | 10.3 | 198.44 | 1.16 |

The total concentration of alkanes, obtained by totaling the average concentrations of each compound, is 103 µg/m³.

In the general category of alkanes, there are compounds with cyclic carbon chain. These are the cycloalkanes (Table 2).

TABLE 2

| Cycloalkane | Formula | $C_A$ (µg/m³) | $MW_A$ (g/mol) | $C_A$ ($ppb_{volume}$) |
|---|---|---|---|---|
| Cyclohexane | $C_6H_{12}$ | 5.6 | 84.16 | 1.49 |
| Methylcyclohexane | $C_7H_{14}$ | 6.6 | 98.19 | 1.50 |
| Methylcyclopentane | $C_6H_{12}$ | 1.6 | 84.16 | 0.42 |

Cycloalkanes represent a small portion of the compounds belonging to this category of alkanes. Their total concentration is 14 µg/m³.

The second category of volatile organic compounds listed is that of the alcohols (Table 3).

TABLE 3

| Alcohol | Formula | $C_A$ (µg/m³) | $MW_A$ (g/mol) | $C_A$ ($ppb_{volume}$) |
|---|---|---|---|---|
| 1-Butanol | $C_4H_{10}O$ | 5.5 | 74.12 | 1.66 |
| 2-Butoxyethanol | $C_6H_{14}O_2$ | 56 | 118.17 | 10.62 |
| 1-Hexanol-2-Ethyl | $C_8H_{18}O$ | 4.1 | 130.23 | 0.7 |
| Phenol | $C_6H_6O$ | 3.4 | 94.11 | 0.8 |

The four main pollutants belonging to this category have individual concentrations that give a total of 69 µg/m³.

The third category is characterised by the aldehyde compounds. These are compounds with individual concentrations that are the highest, in particular formaldehyde and acetaldehyde (Table 4).

TABLE 4

| Aldehyde | Formula | $C_A$ (µg/m³) | $MW_A$ (g/mol) | $C_A$ ($ppb_{volume}$) |
|---|---|---|---|---|
| Formaldehyde | $CH_2O$ | 77.22 | 30.03 | 57.63 |
| Acetaldehyde | $C_2H_4O$ | 28.28 | 44.05 | 14.38 |
| Proprionaldehyde | $C_3H_6O$ | 3.86 | 58.08 | 1.48 |
| Crotonaldehyde | $C_4H_6O$ | 2.52 | 70.09 | 0.8 |
| Butyraldehyde | $C_4H_8O$ | 2.84 | 72.11 | 0.88 |
| Benzaldehyde | $C_6H_7O$ | 2.1 | 106.12 | 0.44 |

The concentrations of each compound of this category are such that their total concentration is 116 µg/m³.

The fourth category is that of the ketones. The three compounds listed in Table 5 have a total concentration of 30.8 µg/m³.

TABLE 5

| Ketone | Formula | $C_A$ (µg/m³) | $MW_A$ (g/mol) | $C_A$ ($ppb_{volume}$) |
|---|---|---|---|---|
| Acetone | $C_3H_6O$ | 26 | 58.08 | 10.03 |
| 2-Butanone | $C_4H_8O$ | 3.4 | 72.11 | 1.05 |
| 4-Methyl-2-pentanone | $C_6H_{12}O$ | 1.4 | 100.16 | 0.3 |

Aromatics are the compounds belonging to the fifth category. This category also includes a compound with a high concentration, namely toluene (Table 6).

TABLE 6

| Aromatic | Formula | $C_A$ (µg/m³) | $MW_A$ (g/mol) | $C_A$ ($ppb_{volume}$) |
|---|---|---|---|---|
| Benzene | $C_6H_6$ | 4.43 | 78.12 | 1.27 |
| Toluene | $C_7H_8$ | 62.32 | 92.15 | 15.15 |
| o-xylene | $C_8H_{10}$ | 3.93 | 106.17 | 0.82 |

TABLE 6-continued

| Aromatic | Formula | $C_A$ (µg/m³) | $MW_A$ (g/mol) | $C_A$ ($ppb_{volume}$) |
|---|---|---|---|---|
| Styrene | $C_8H_8$ | 0.92 | 104.15 | 0.19 |
| Ethylbenzene | $C_8H_{10}$ | 5.99 | 106.17 | 1.26 |
| 2-Ethyltoluene | $C_9H_{12}$ | 2.3 | 120.19 | 0.42 |
| 3-Ethyltoluene | $C_9H_{12}$ | 3.7 | 120.19 | 0.69 |
| 4-Ethyltoluene | $C_9H_{12}$ | 1.9 | 120.19 | 0.35 |
| 1,2,4-Trimethylbenzene | $C_9H_{12}$ | 0.7 | 120.19 | 0.13 |

The total concentration of aromatic compounds is 86 µg/m³.

The last category covers the terpene compounds (Table 7). Their total concentration is 76.8 µg/m³.

TABLE 7

| Terpene | Formula | $C_A$ (µg/m³) | $MW_A$ (g/mol) | $C_A$ ($ppb_{volume}$) |
|---|---|---|---|---|
| Pinene | $C_{10}H_{16}$ | 18.3 | 136.23 | 3.01 |
| Limonene | $C_{10}H_{16}$ | 58.5 | 136.23 | 9.62 |

The total concentration of volatile organic compounds is 420 µg/m³.

This non-exhaustive list of pollutants shows that their average concentration is lower than $ppm_{volume}$. During the analysis of the experimental results on the complex mixes at low concentrations, it was observed that each pollutant undergoes the purification process by photocatalysis upon contact with titanium dioxide as if it were the only pollutant in the test chamber. This property is used to introduce all above-mentioned compounds into an algorithm for sizing the purification device. When using this property, a test pollutant A is defined, with an initial concentration that is the total concentration of VOCs, i.e. 420 µg/m³.

The parameters in the above-mentioned purification model could be precisely defined in the case of acetaldehyde purification. These parameters, the quantum efficiency and the reference concentration, depend on the photon flux reaching the titanium dioxide. On the basis of the three values of the parameters, determined for a photon flux of $1.66*10^{-4}$, $7.26*10^{-5}$ and $2.56*10^{-5}$ einstein/m²/s, respectively, an interpolation function is defined for the quantum efficiency and the reference concentration. These interpolation functions allow to obtain the value of the purification parameters as a function of photon flux. The accuracy of the values is ensured in so much as the incident photon flux is between $1.66*10^{-4}$ and $2.56*10^{-5}$ einstein/m²/s.

Precise knowledge of the purification parameters for acetaldehyde makes this compound the test pollutant allowing to introduce all VOC compounds cited in the lists above.

The purification device according to the invention is thus sized assuming an atmosphere only polluted with acetaldehyde at a concentration of 420 µg/m³, which corresponds to 213 $ppb_{volume}$. In order to ensure a safety margin for sizing, the concentration of acetaldehyde is assumedly 1 $ppm_{volume}$.

During the analysis of the experimental results, no intermediate product appeared in the decomposition process of the acetaldehyde upon contact with the film of spray-deposited titanium dioxide. The only decomposition reaction considered is therefore the decomposition reaction of acetaldehyde by hydroxyl radicals.

The use of our theoretical purification model as a limiting condition in the overall calculation of the dispersion of acetaldehyde in the purification wall requires to determine purification parameters that are obtained by interpolation functions on values determined elsewhere (not published), the determination of stoichiometric coefficients obtained by means of the equation for the acetaldehyde decomposition and the determination of the photon flux reaching the titanium dioxide surface.

7.1 Photon Flux

The evaluation of the photon flux is an important step in the optimisation algorithm. For this calculation, a visual calculation software is used, for example the SPEOS software (Optis, France). This software determines illumination charts and light flux charts by calculating the propagation of light rays according to the laws of physics. These charts allows to define the spatial function of the distribution of light intensity over a given surface ($F_{SPEOS}$):

$$F_{SPEOS}(x,y) = {}_{total\_spectrum}\!\int I(\lambda,x,y)d\lambda \qquad (1.7)$$

where:
- x,y are the spatial coordinates given to a point on the surface;
- total_spectrum is the total emission spectrum of the lamps used;
- I is the light intensity (W/m²/nm);
- λ is the wavelength of the radiation (nm).

For our theoretical purification model, the photon flux must be determined, i.e. the number of photons reaching the illuminated surface at a coordinate point (x,y) per unit of time.

In order to link the data obtained from the illumination charts and the number of photons ($N_{hv}$), the following hypothesis is followed: the light intensity I (λ,x,y) may be separated into three contributing elements; the first is the standard of light intensity |I|, the second only depends on the spatial position of the point on the surface considered $\bar{I}_s(x,y)$ and the third represents the spectral dependency $\bar{I}_\lambda(\lambda)$. The last two values are normalized. We have:

$$I(\lambda,x,y) = |I|\bar{I}_s(x,y)\bar{I}_\lambda(\lambda) \qquad (1.8)$$

By introducing this definition of the light intensity (1.8), the equation of the photon flux reaching the point x,y of the illuminated surface is re-written as:

$$\frac{dN_{hv}(x,y)}{dt} = \frac{|I|\bar{I}_s(x,y)}{N_{Avogadro}}\left[\int_0^{\lambda_{gap}} \frac{\bar{I}_\lambda(\lambda)}{E_{hv}(\lambda)}d\lambda\right], \qquad (1.9)$$

where E(hv)=hv=h.c/λ.

The integral on the wavelengths that can be absorbed by the semiconductor may be evaluated when the emission spectrum of the source is known (generally provided by the company manufacturing the lamp). For lamps of CLEO type from the firm Philips, it was noted that there is a diminution of the light intensity depending on the distance between the illumination system and the surface illuminated. When the spectra are normalized, the emission spectrum for the lamp provided by the manufacturer is obtained.

A normalized photon flux ($F_{hv,0}$), that can only be calculated from the data supplied by the manufacturer and that is constant over the entire illuminated surface, is thus defined as:

$$\bar{F}_{hv,0} = \frac{1}{N_{Avogadro}}\left[\int_0^{\lambda_{gap}} \frac{\bar{I}_\lambda(\lambda)}{E_{hv}(\lambda)}d\lambda\right] = 9.695 \times 10^{-14} \qquad (1.10)$$

If the ratio (1.8) is also introduced in the expression (1.7), the following expression of the function $F_{SPEOS}$ is obtained:

$$F_{SPEOS}(x,y) = |I|\bar{I}_s(x,y)_{total\_spectrum}\!\int \bar{I}_\lambda(\lambda)d\lambda \qquad (1.11)$$

In this expression (1.11), a term that may be directly calculated from the data of the manufacturer of the light source is once more obtained:

$$\bar{I}_{source,0} = {}_{total\_spectrum}\!\int \bar{I}_\lambda(\lambda)d\lambda = 3.909 \times 10^{-8} \qquad (1.12)$$

When introducing the expressions (1.10, 1.11, 1.12) into the calculation of the number of photons reaching the illuminated surface per unit of time (1.9), the formula is:

$$\frac{dN_{hv}(x,y)}{dt} = F_{SPEOS}(x,y)\frac{\bar{F}_{hv,0}}{\bar{I}_{source,0}} \qquad (1.13)$$

(where $\bar{F}_{hv,0}/\bar{I}_{source,0} = 2.48*10^{-6}$).

When using this formula (1.13), the illumination charts provided by the SPEOS software ($F_{SPEOS}(x,y)$) and the spectral data for the light source, the photon flux reaching each point on the surface of the catalyst can be calculated.

7.2 Illumination Charts

In the preceding paragraph, it was shown that on the basis of an illumination chart obtained with the SPEOS software and of the spectral characteristics of the light sources, all the useful data for our purification model are available.

In order to obtain the illumination charts, a three-dimensional model of the purification wall is introduced into the SPEOS software. As for the geometrical models used for flow simulations, the essential elements, the important elements and the negligible elements are determined. Nevertheless, the elements defined in each of the three categories are different from those defined within the context of the CFD (Computational Fluid Dynamics) calculation. The aims of CFD simulations and those of SPEOS software being different, it is usual to differently list the elements of the three categories.

The 25 W UVA lamps of CLEO type and the front and back parts of the purification device are included in the essential elements, i.e. the elements with geometrical characteristics and spatial positions that may not differ from reality.

The purification grates are included in the important elements, i.e. the elements that must be taken into account in the geometrical model but that may be described with a geometry and spatial position that differ from reality. The thickness of the grate of 3 mm does not play a central part in the illumination calculation. The shadows that may be caused by the thickness of the grate may be ignored. The grates are assumedly two-dimensional flat surfaces.

The fans, the top and bottom parts as well as the vertical sides of the wall, the electric box with the supply for the different electric systems, . . . are included in the negligible elements, i.e. the elements whose influence on the aim of the simulation is negligible. The fans, the electric box, . . . are ignored since the materials of which they are made have a very short reflective index in the range of UVAs, which means that the quantity of energy reflected back towards the surfaces of the grates covered with titanium dioxide is negligible. For the top, bottom and side parts of the wall, we assume that their impact on the illumination of the grates, which are perpendicular to them, is also negligible.

Once the elements of our geometrical model are defined, the parameters required for the simulation are introduced. All surfaces are characterised by physical properties relating to the subject of light: the type of light reflection to be considered, Lambertian, Gaussian or other, . . . , which depends on the state of the surface of the material; the spectral dependency of reflectivity; etc. For light sources, their emission spectra and their power are introduced.

Simulations using the SPEOS software must provide the quantity of energy reaching each point on each expanded metal grate. To obtain this information, further processing must be performed on the illumination charts. Indeed, the illumination charts are simple flat, two-dimensional surfaces that "count" the number of light rays crossing them at a point so as to deduce the quantity of energy at the point under consideration (FIG. 5.a). Similarly, the SPEOS software allows to draw profiles of light intensity reaching the grate by direct and indirect illumination (see example in FIG. 5.b).

The further processing simply consists in projecting the raw illumination chart on the actual surface of the expanded metal grate. This operation is simply performed by multiplying the raw illumination chart by a function $\Gamma(x,y)$ of zero everywhere except where the expanded metal is located, in which case it equals one. The charts of light intensity to introduce into our purification model are obtained (FIG. 6).

Two methods for introducing these intensity charts are available:
1) introduce all the data into a file that will be used in the calculation code;
2) define a mathematical function that describes the spatial distribution of the light intensity.

The second method is opted for since it allows to obtain analytical solutions in specific conditions. The mathematical function has the following form:

$$F_{SPEOS}(x,y) = \Gamma(x,y) \Re \left[ \int g(k_x,k_y) \exp[i(k_x x + k_y y)] dk_x dk_y \right] \quad (1.14)$$

where:
$F_{SPEOS}$ is the spatial function describing the distribution of light intensity on the surface under consideration;
x,y are the coordinates of the point under consideration on the illuminated surface;
$g(k_x,k_y)$ is the Fourier transform of the function $F_{SPEOS}$;
$k_x, k_y$ are the numbers of waves according to x,y ($2\pi/\lambda_x$, $2\pi/\lambda_y$), respectively;
$\Re$ is the real part of the integral;
$\Gamma(x,y)$ is the projection function of the raw illumination chart on the actual surface of the expanded metal.

This is a Fourier integral. This function $F_{SPEOS}(x,y)$ is used in our purification model. For any distribution of light intensity, the flat waves of amplitude $g(k_x,k_y)$ must be integrated over the total number of waves $(0,\infty)$. In our study, this Fourier integral may be simplified to a Fourier series since the geometrical characteristics of the system studied allow to define periodicity.

In a first approximation, the light intensity is assumedly constant horizontally, which removes the dependency on x in the Fourier integral. In addition, the periodicity of the lamps according to y allows to replace the integral by a total of the wavelengths multiples of the distance between two lamps.

$$F_{SPEOS}(x,y) = \Gamma(x,y) \sum A_j \cos\left( j \frac{2\pi}{d_{lamp}} y \right) \quad (1.15)$$

where $A_j$ represents the amplitude of the wave j, $d_{lamp}$ represents the distance between two rows of lamps.

In general, this total relates to an infinite number of contributing elements. In some cases, only the contributing elements of the first few modes are significant, which allows to reduce the infinite total to a total of a finite number of modes.

To obtain the function $F_{SPEOS}$, a Fourier analysis is therefore performed on the raw illumination charts provided by the simulations with the SPEOS software. This analysis gives the only parameters not defined in the expression (1.15), namely the coefficients $A_j$ of the Fourier decomposition.

7.3 Evolution Equation and Limiting Conditions

The aim of the purification device is to continuously purify the volume of air of a space under consideration. The efficiency of the purification device must therefore be studied in stationary mode. The evolution equations for the concentration of acetaldehyde are therefore stationary evolution equations (equation of advection-diffusion):

$$\nabla \cdot (\vec{u} C_A) = \nabla \cdot [D_A(T,p^{tot},\mu^t) \nabla C_A] \quad (1.16)$$

where $\vec{u}$ (m/s) is the range of air speed, $C_A$ (kg/m$^3$) is the concentration of pollutant A, $D_A$ is the diffusion coefficient of the pollutant A, made up of a molecular contributing element and of a turbulent contributing element, with T(K) being the air temperature, $p^{tot}$(atm) the total pressure and $\mu^t$ the turbulent viscosity.

On the internal parts of the external frame of the purification wall, the elimination of the mass flow is preserved as a limiting condition. On the expanded metal grates, our purification model is introduced for acetaldehyde. The introduction of the data from the SPEOS software and the interpolation functions of the purification parameters allows to specify the expression for the decrease of acetaldehyde over time.

For the study of the sizing of the purification wall, a concentration at the wall intake must be applied. Since the efficiency of the purification device in stationary mode is to be calculated, a constant concentration equal to 1 ppm$_{volume}$ is applied. At the outlet, no condition is applied.

7.4 Definition of the Efficiency of the Purification Device

In order to size the purification device, a criterion must be defined to allow the evaluation of the purification performance. To do so, the pollutant flow rate entering and leaving the device is defined as:

$$Q_{A,intake-outlet} = S_{intake}-S_{outlet} \int\int C_A \vec{u} \cdot \vec{n} \, dS \quad (1.17)$$

where
$Q_{A,intake-outlet}$ is the flow rate of the pollutant at the intake or outlet of the purification device;
$C_A$ is the concentration of the pollutant at the intake or outlet of the purification device;
$\vec{u}$ is the speed range at the intake or outlet of the purification device;
$\vec{n}$ is the normal at the surface under consideration pointing towards the inside of the purification device at the intake and towards the outside at the outlet.

Based on the flow rate of the pollutant, the efficiency of the purification wall for the pollutant A ($\eta_{A,wall}$) is defined as:

$$\eta_{A,wall} = \frac{Q_{A,outlet} - Q_{A,intake}}{Q_{A,intake}} \quad (1.18)$$

This definition (1.18) allows to have a value varying between 0, when the system is totally inefficient, and 1, when the system is perfectly efficient, which corresponds to a purification device reintroducing no pollutant into the space to be cleaned.

Figure 7:
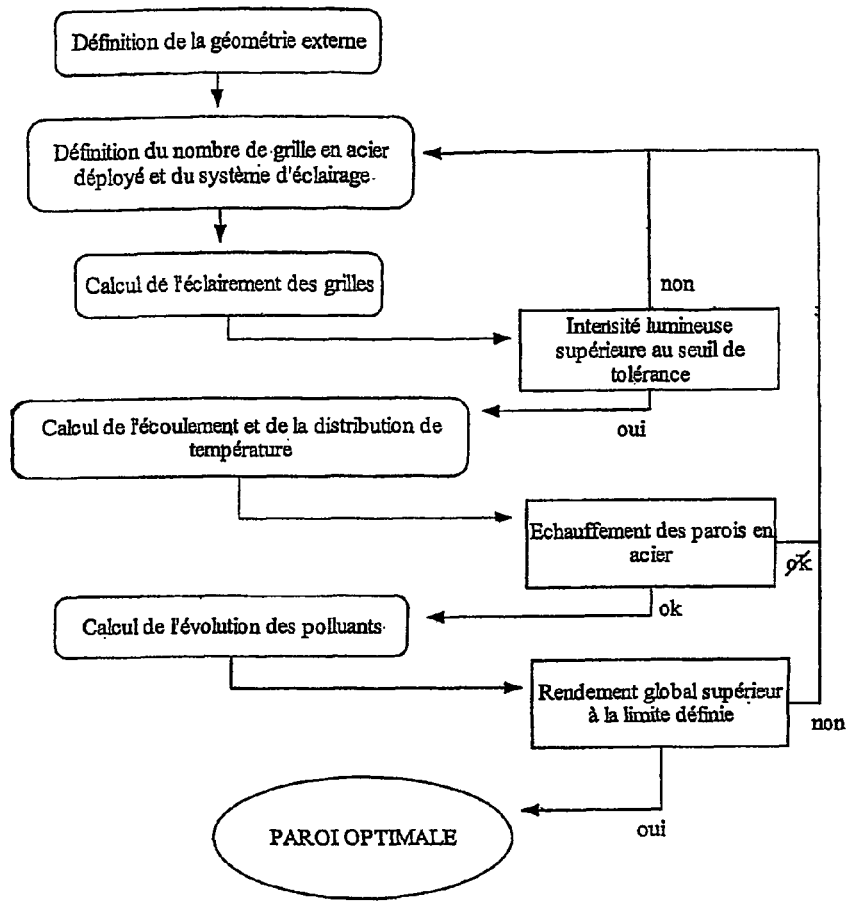
FIG. 7 shows the algorithm for optimising the sizing of the purification wall according to the present invention.

FIG. 7 summarises the optimisation algorithm of the purification device.

7.5 Two-Dimensional Approach

The geometry of the purification wall allows the problem to be tackled with a two-dimensional approach instead of a complete three-dimensional approach. The speed component along the $\vec{e}_y$ axle (FIG. 1) is negligible compared to the vertical and horizontal speeds along the $\vec{e}_x$ axle. The study of the purification device is performed across a vertical section. The three-dimensional effects are negligible across the entire width of the wall except at the two ends where the effect of the two vertical side walls can be felt. In a first study, these 3D effects are ignored so as to assume a two-dimensional flow in the entire wall.

This two-dimensional approach allows to use a calculation code developed for the 2D case.

In the description of the wall, the size of the expanded metal meshes on which the catalyst, $TiO_2$, is deposited has been defined. The expanded metal grates are positioned in the plane O, $\vec{e}_y$, $\vec{e}_z$, which is the plane perpendicular to the vertical section defined to provide a two-dimensional approach for the flow. To model the expanded metal, its main effect must be referred to. The expanded metal is used for depositing titanium dioxide. The main characteristic that must be preserved in the model is the ratio ($S_{steel}$) between the surface of the expanded metal and the total surface of the grate.

The expanded metal is modelised as a perforated wall with aperture sizes that are such that the surface ratio is preserved (FIG. 8: 1 grate and 3 lamps). For an active wall with $n_{grates}$ expanded metal grates, a total surface of titanium dioxide is obtained equal to:

$$S_{TiO2} = 2 n_{grate} S_{steel} H_{wall} L_{wall} \qquad (1.19)$$

The factor 2 expresses the fact that the titanium dioxide is deposited on both sides of the grate.

FIG. 9 synthesizes the efficiency curves of the purification wall as a function of the number of rows of UVA lamps, depending on whether one or two grates are used and whether there is natural or forced ventilation. The highest efficiency is achieved with the greatest number of rows of lamps (4 lamps), two grates and natural ventilation.

The use of a UVA flux as activator of the $TiO_2$ film causes an increase in temperature inside the purification wall. In order to determine the profiles of temperature increase on the external facings, CFD software allowing the calculation of the flow and temperature ranges was used, taking into account the flows of radiative, convective and conductive heat. FIG. 10 gives examples of temperature increases $\Delta T = T - T0$ as a function of the height y of the wall, depending on the number of lamps and depending on natural or forced convection.

The invention claimed is:

1. Device for the continuous photocatalytic purification of the air of an inhabited room, in the form of a wall element (1), comprising:
    an external metal structure, preferably made of steel;
    an opening (11) for the intake of air to be treated, located at the bottom of the front part (10) of the wall element (1);
    an internal metal frame (4) to which a series of UVA lamps (3) are attached;
    a filter (2) comprising a grate covered by a film with photocatalytic titanium dioxide ($TiO_2$);
    an opening (12) for the outlet of the purified air, located at the top of the front part (10) of the wall element (1), the airflow inside the device being ensured by natural circulation or forced circulation with at least one fan (5);
    characterised in that said device comprises at least one grate made of expanded metal covered by a film with titanium dioxide ($TiO_2$) mainly in the anatase phase, so as to maximise the surface of the photocatalyst illuminated by the UVA light;
    wherein the at least one grate is arranged vertically, substantially parallel to the external metal structure, and supported only by fixings on the perimeter of the at least one grate.

2. Device according to claim 1, characterised in that the external metal structure is made of steel or has an internal surface covered by a thin layer with a reflective index greater than 90% for wavelengths shorter than 400 nm.

3. Device according to claim 2, characterised in that the external metal structure is made of bright-annealed stainless steel.

4. Device according to claim 1, characterised in that the front part (10) of the external structure has a width of at least 1.5 meters, preferably 2 meters, and in that the intake and outlet openings (11,12) for the air are in the form of slits of equal width and of a length slightly shorter than that of said front part (10) and of a height greater than 3 cm, preferably equal to 5 cm.

5. Device according to claim 4, characterised in that said openings (11,12) are positioned less than 10 cm, preferably 5 cm, from the top and bottom ends of said front part (10), respectively.

6. Device according to claim 1, characterised in that the expanded metal is an expanded steel and in that the entire surface of the meshes (6) of this expanded steel ($S_{steel}$) is covered with the $TiO_2$ film, with the exception of the surface of the thickness of the mesh, said surface other meshes of the expanded steel ($S_{steel}$) being defined as:

$$S_{steel} = \left[ ws_{mesh} \sqrt{\left(\frac{LD_{mesh}}{2}\right)^2 + \left(\frac{SD_{mesh}}{2}\right)^2} - \frac{ws_{mesh}^2}{2\sin\left(2\mathrm{arctg}\left(\frac{SD_{mesh}}{LD_{mesh}}\right)\right)} \right]$$

where $LD_{mesh}$, $SD_{mesh}$ and $ws_{mesh}$ are respectively the long diagonal, the short diagonal and the strip of the mesh.

7. Device according to claim 6, characterised in that the mesh (6) is selected to minimise the ratio ($s_{steel}$) between its physical surface ($S_{steel}$) and its total surface ($S_{mesh}$):

$$s_{steel} = \frac{S_{steel}}{S_{mesh}} = \frac{4}{LD_{mesh} SD_{mesh}} S_{steel}$$

said ratio preferably being ⅓.

8. Device according to claim 1, characterised in that the UVA lamps (3) are arranged in series of three across the width of the wall element (1).

9. Device according to claim 1, characterised in that the fan (5) is of a tangential type set at 90° and is located at the top of the wall element (1), the number of fans being selected to ensure that at least 30 m³/hour/person of air is renewed in an inhabited room.

10. Device according to claim 1, characterised in that it has the form of a cylinder of circular, rectangular or square cross-section with at least one UVA lighting tube along the axle of the cylinder and surrounded by an expanded metal grate covered by photocatalytic TiO$_2$, the internal surface of the cylinder having an reflective index greater than 90%.

11. The device of claim 10, wherein the air purification device is in the form of an air duct.

12. The device of claim 1, wherein the air purification device is implemented in the construction sector, in the form of a structural or decorative element such as a wall panel, dividing wall, floor, ceiling or false ceiling, said element having an external metal surface covered with a finish such as plaster, paint or wallpaper.

13. Device according to claim 1, wherein the air enters the wall element (1) through the opening (11) at the bottom of the front part (10) and exits via the opening (12) at the top of the front part (10), wherein an air flow path in the wall element (1) is substantially parallel to the filter (2).

14. Device according to claim 1, wherein the internal metal frame (4) is arranged substantially parallel to the filter (2), wherein the series of UVA lamps (3) are arranged between the at least one grate and the external metal structure.

15. Device according to claim 1, wherein the filter has a vertical span extending substantially parallel to the external metal structure, and a horizontal span, wherein the vertical span is substantially larger than the horizontal span.

16. Device according to claim 1, wherein the at least one grate having a front surface and a back surface, wherein the front and back surfaces are free of any support structure.

17. Device according to claim 16, wherein the at least one grate is configured to have a sufficient structural rigidity to maintain the vertical arrangement, supported only by fixings on the perimeter.

18. Device according to claim 1, wherein the UVA lamps are attached directly on the internal metal frame, wherein the series of UVA lamps are arranged adjacent the filter, such that the UVA lamps are not between the at least one grate.

19. Device according to claim 18, wherein the UVA lamps are arranged in a same plane as the at least one grate.

20. Method for optimising the sizing of an air purification element according to claim 1, characterised by the following steps:
  a) definition of the external geometry of the device;
  b) definition of the number of grates made of expanded steel and of the illumination device (3);
  c) calculation of the illumination of the grates; if the light intensity is not greater than the set threshold, return to step b);
  d) calculation of the airflow and of the temperature distribution; if front and back parts (10,15) of the wall element (1) heat up, return to step b);
  e) calculation of the change in the pollutant concentration; if the overall efficiency of purification is not greater than the predefined limit, return to step b);
  achieving the purification or pollution-removal element with optimum dimensions.

\* \* \* \* \*